(12) United States Patent
Tawil et al.

(10) Patent No.: US 11,173,071 B1
(45) Date of Patent: Nov. 16, 2021

(54) PERIOCULAR DRESSING SYSTEM AND COMPOSITION

(71) Applicants: Ahmad H. Tawil, Dallas, TX (US); Ronald Mancini, Dallas, TX (US)

(72) Inventors: Ahmad H. Tawil, Dallas, TX (US); Ronald Mancini, Dallas, TX (US)

( * ) Notice: Subject to any disclaimer, the term of this patent is extended or adjusted under 35 U.S.C. 154(b) by 459 days.

(21) Appl. No.: 16/290,031

(22) Filed: Mar. 1, 2019

Related U.S. Application Data

(60) Provisional application No. 62/637,055, filed on Mar. 1, 2018.

(51) Int. Cl.
| | |
|---|---|
| *B32B 3/10* | (2006.01) |
| *A61F 13/00* | (2006.01) |
| *B32B 27/40* | (2006.01) |
| *B32B 7/12* | (2006.01) |
| *A61F 7/02* | (2006.01) |
| *B32B 27/12* | (2006.01) |
| *A61F 13/02* | (2006.01) |
| *A61K 38/12* | (2006.01) |
| *A61K 36/28* | (2006.01) |
| *A61K 38/48* | (2006.01) |
| *A61K 35/644* | (2015.01) |
| *A61K 9/70* | (2006.01) |
| *B32B 5/02* | (2006.01) |
| *A61F 7/00* | (2006.01) |

(52) U.S. Cl.
CPC .......... *A61F 13/00063* (2013.01); *A61F 7/02* (2013.01); *A61F 13/0233* (2013.01); *A61F 13/0266* (2013.01); *A61K 9/7084* (2013.01); *A61K 35/644* (2013.01); *A61K 36/28* (2013.01); *A61K 38/12* (2013.01); *A61K 38/4873* (2013.01); *B32B 5/022* (2013.01); *B32B 7/12* (2013.01); *B32B 27/12* (2013.01); *B32B 27/40* (2013.01); *A61F 2007/0004* (2013.01); *A61F 2007/0219* (2013.01); *A61F 2007/0244* (2013.01); *A61F 2013/00285* (2013.01); *B32B 2307/7145* (2013.01); *B32B 2535/00* (2013.01)

(58) Field of Classification Search
None
See application file for complete search history.

(56) References Cited

U.S. PATENT DOCUMENTS

| | | | |
|---|---|---|---|
| 2006/0182787 A1* | 8/2006 | Jaenichen | C08L 75/04 424/445 |
| 2007/0009583 A1* | 1/2007 | Qvist | A61L 15/44 424/445 |
| 2011/0190722 A1* | 8/2011 | Munro | A61L 15/425 604/367 |
| 2015/0079134 A1* | 3/2015 | Gause | A61K 39/0003 424/265.1 |
| 2016/0220722 A1* | 8/2016 | Wardell | A61K 33/30 |

(Continued)

*Primary Examiner* — Christopher M Polley
(74) *Attorney, Agent, or Firm* — Leavitt Eldredge Law Firm

(57) ABSTRACT

A periocular dressing includes a base layer composed of a nonwoven material; a top layer having a composition bound to a polyurethane film, the composition including a hydrogel with a percentage by weight of bacitracin, the top layer to come into contact with a user's skin; and a removable membrane secured over the top layer and to be removed; the polyurethane film of the top layer is adhesively secured to the base layer; and the top layer promotes vasoconstriction and antibacterial properties.

3 Claims, 3 Drawing Sheets

(56) References Cited

U.S. PATENT DOCUMENTS

2016/0250373 A1* 9/2016 Munro .................... A61L 15/26
　　　　　　　　　　　　　　　　　　　　　602/48
2018/0042789 A1* 2/2018 Bradford ............. A61F 13/0253

* cited by examiner

PERIOCULAR DRESSING SYSTEM AND COMPOSITION

BACKGROUND

1. Field of the Invention

The present invention relates generally to dressing, and more specifically, to a periocular dressing system with antibacterial properties and configured to provide cold compression for the user.

2. Description of Related Art

Wound dressings are well known in the art and are effective means to assist in healing. It is conventional to utilize low temperature solutions to promote vasoconstriction which limits ecchymosis and edema during treatment. However, external, non-sterile sources of cold compression provide a potential source of infection, as they are often placed directly on to wound healing sites.

Accordingly, it is desirable and an objective of the present invention to provide a periocular dressing that provides sterile cold compression in a convenient system.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
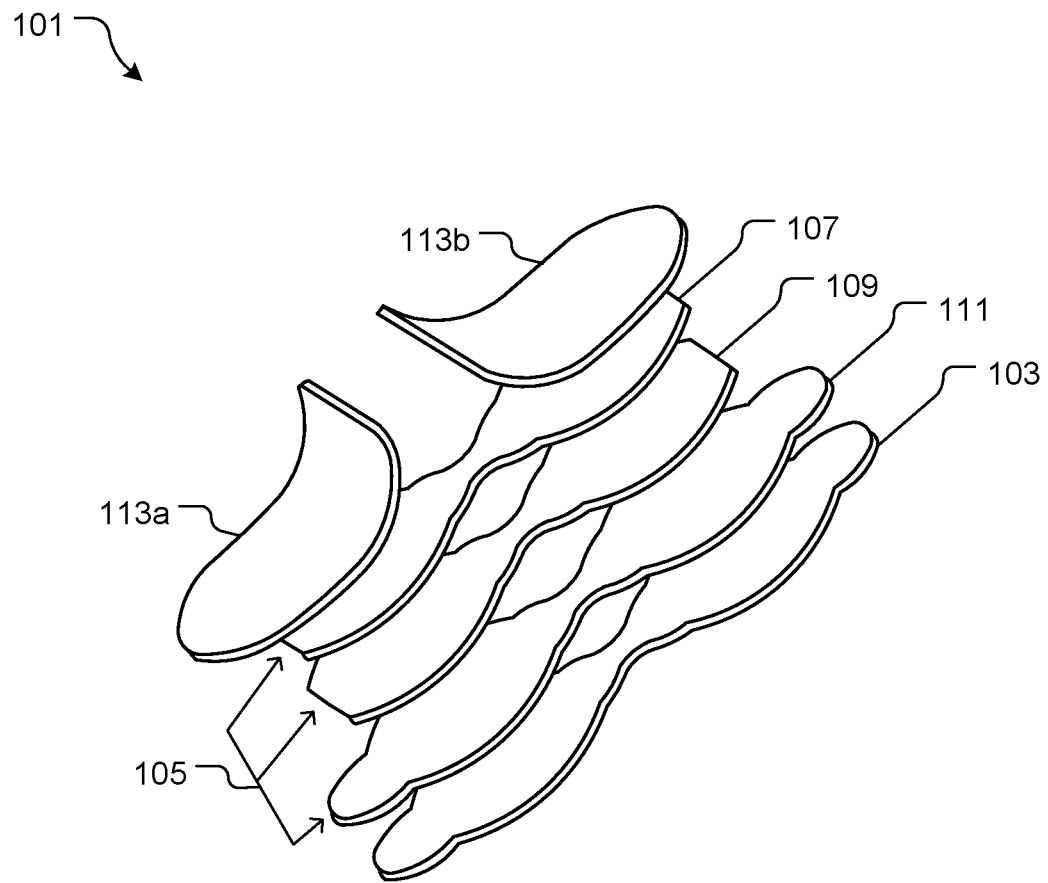
FIG. 1 is an exploded view of a periocular dressing system in accordance with a preferred embodiment of the present application.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional dressing systems. Specifically, the present invention provides for a convenient periocular dressing system that provides for an antibacterial hydrogel layer for improved hygiene. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Referring now to the drawings wherein like reference characters identify corresponding or similar elements throughout the several views, FIG. 1 depicts an exploded view of a dressing system 101 in accordance with a preferred embodiment of the present application. It will be appreciated that system 101 overcomes one or more of the above-listed problems commonly associated with conventional dressing systems.

In the contemplated embodiment, system 101 includes a base layer 103 composed of a nonwoven fabric that is flexible and will not come into contact with the user's skin. System 101 further includes a top layer 105 that includes a hydrogel layer 107 with ingredients as will be discussed in further detail below. The hydrogel layer 107 is bound to a polyurethane film 109 which is adhesively bound to the base layer 103 via one or more adhesives 111. In the preferred embodiment, the hydrogel layer 107 is covered with a removable film 113a-b, such as a polyethylene membrane. In some embodiments, the dressing system 101 is secured within a foil blister package for sanitation and easy removal for use.

It should be appreciated that one of the unique features believed characteristic of the present application is the hydrogel layer that includes unique ingredients and is sealed by the film 109, thereby providing for improved sanitation. The dressing system will provide a sterile barrier for the contours of the periocular region and the antibacterial properties help ensure the blocking and prevention of infection around the region.

Figure 2:
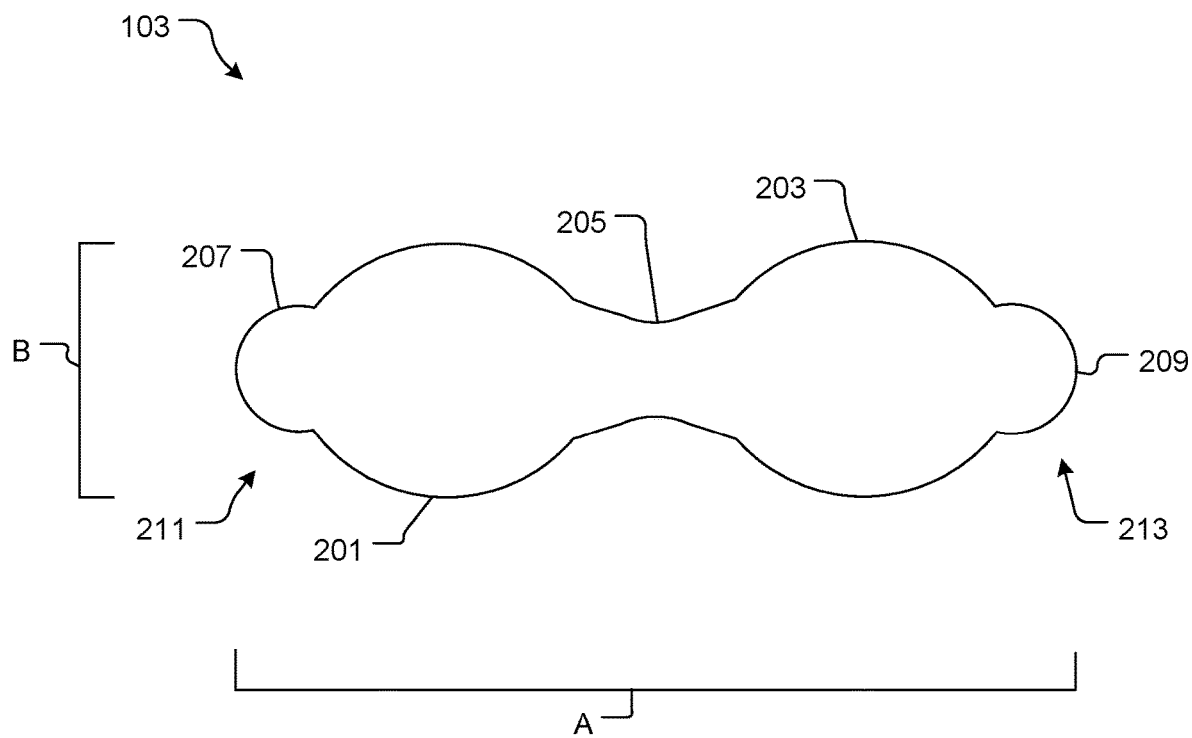
FIG. 2 is a top view of the base layer of the system of FIG. 1.

In FIG. 2, a top view of the base layer 103 is shown to show the shape and dimensions of the preferred embodiment. In the preferred embodiment, the base layer 103 includes a body formed by a first oval portion 201 connected to a second oval portion 203 via a bridge 205. In addition, first and second tabs 207, 209 are positioned to extend from the first end 211 and the second end 213. It should be appreciated that the exact dimensions can vary, however, in one embodiment, the total length of the body is approximately 230 mm and the total height of the body is approximately 80 mm, as shown with brackets A and B respectively.

Figure 3:
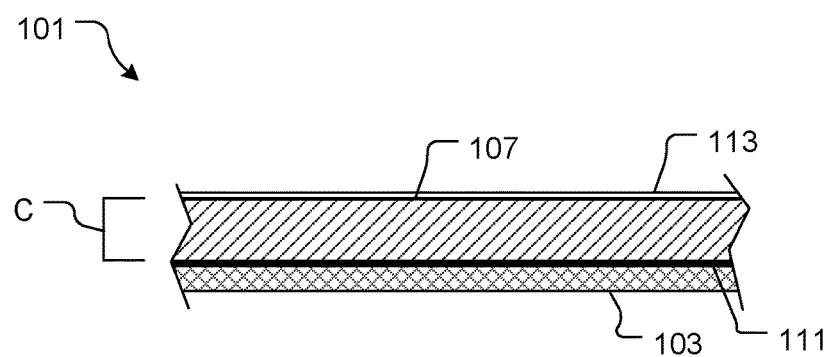
FIG. 3 is a cross sectional view of the layers of the system of FIG. 1.

In FIG. 3, a cross sectional view of the dressing system 101 is shown. The layers are shown secured together, wherein the hydrogel layer 107 is secured to the base layer 103 via an adhesive 111 and covered with a film 113. As shown, in one embodiment, the hydrogel layer 107 is approximately 3 mm in depth (C), however, it should be appreciated that the exact dimensions can vary based on manufacturing and functional considerations.

Figure 4:
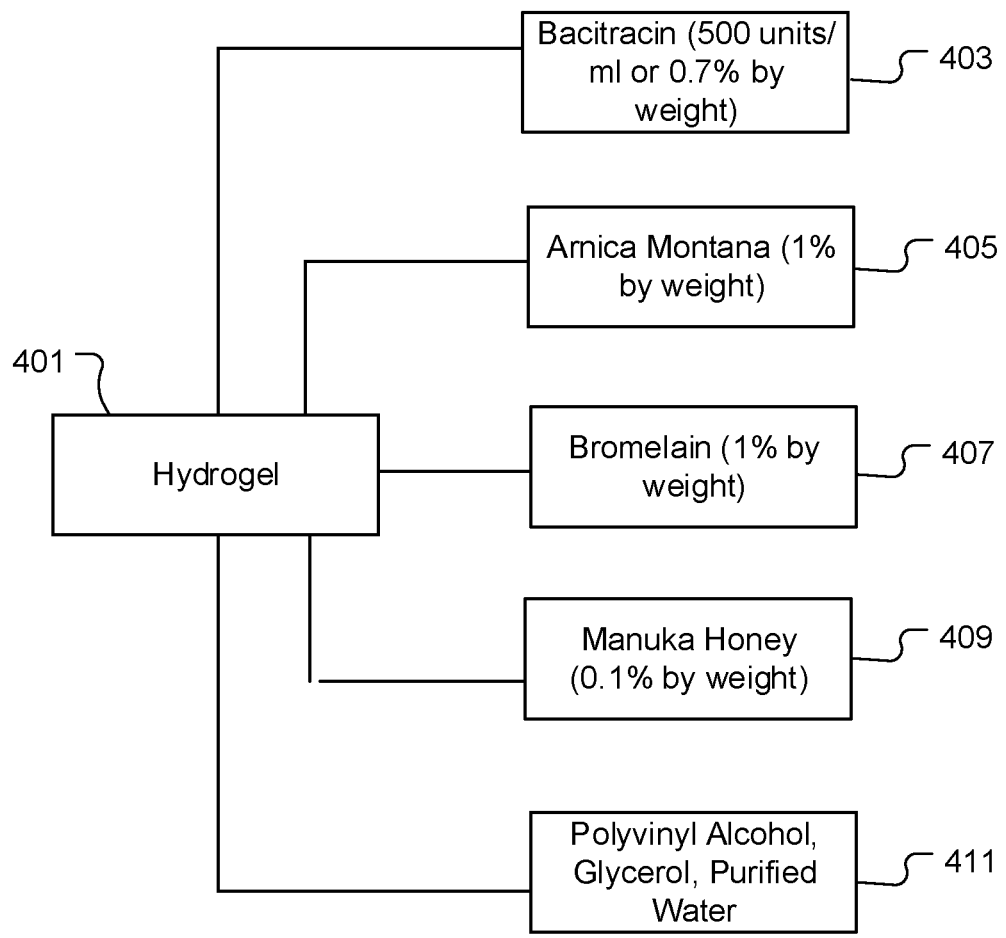
FIG. 4 is a simplified schematic of the components of a hydrogel layer of FIG. 1.

In FIG. 4, a simplified schematic depicts the composition of the hydrogel 401 in the preferred embodiment. It should again be appreciated that the exact ingredients can vary, however, it has been tested and determined that the list shown herein provides for user benefits and healing. In the preferred embodiment, the hydrogel 401 includes bacitracin 403 at a 0.7% by weight amount, arnica montana 405 at a 1% by weight amount, bromelain 407 by 1% by weight amount, and manuka honey 409 at 0.1% by weight. It should be appreciated that the hydrogel 401 can include additional fillers as is known in the art, including polyvinyl alcohol, glycerol, and purified water 411.

It should be appreciated that hydrogel maintains a cool temperature after refrigeration, thereby providing an effective agent for promotion of vasoconstriction after surgical procedures. The addition of antibacterial bacitracin acts as a safeguard to minimize bacterial contamination of the wound location. In addition, the homeopathic additives, such as arnica montana, bromelain, and manuka honey are thought to act as potentially beneficial agents in speeding resolution of ecchymosis. The combination of ingredients provides for an improved dressing system over the current state of the art.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A periocular dressing comprising:
    a base layer composed of a nonwoven material;
    a top layer having a composition bound to a polyurethane film, the composition including a hydrogel with 0.7 percent by weight of bacitracin, 1 percent by weight of arnica montana, 1 percent by weight of bromelain, and 0.1 percent by weight of Manuka honey, the top layer to come into contact with a user's skin; and
    a removable membrane secured over the top layer and to be removed;
    wherein the polyurethane film of the top layer is adhesively secured to the base layer; and
    wherein the top layer promotes vasoconstriction and antibacterial properties.

2. The dressing of claim 1, wherein the base layer further comprises:
    a body having a first oval shaped portion connected to a second oval shaped portion by a bridge, and further having a first tab extending from a first end and a second tab extending from a second end.

3. The dressing of claim 1, wherein the hydrogel is approximately 3 mm thick.

* * * * *